United States Patent [19]

Hicks

[11] Patent Number: 5,354,994
[45] Date of Patent: Oct. 11, 1994

[54] METHOD AND APPARATUS FOR DETECTING FILM EDGES AND FILM OPTICAL CENTERS

[76] Inventor: Ray Hicks, 4444 W. Bristol Rd., Flint, Mich. 48507

[21] Appl. No.: 11,961

[22] Filed: Feb. 1, 1993

Related U.S. Application Data

[63] Continuation-in-part of Ser. No. 816,135, Dec. 31, 1991, abandoned.

[51] Int. Cl.⁵ .......................................... G01N 21/86
[52] U.S. Cl. ................... 250/561; 353/26 A
[58] Field of Search ............... 250/559, 560, 561, 570, 250/571; 353/26 A; 355/41

[56] References Cited

U.S. PATENT DOCUMENTS

| | | | |
|---|---|---|---|
| 2,888,260 | 5/1959 | Schowerer | 271/2.6 |
| 3,123,195 | 3/1964 | Hewitt et al. | 197/133 |
| 3,124,289 | 3/1964 | Lynch et al. | 226/1 |
| 3,184,177 | 5/1965 | Hannah | 242/55 |
| 3,209,644 | 10/1965 | Simmon et al. | 88/24 |
| 3,515,883 | 6/1970 | Akamatsu | 250/214 |
| 4,167,678 | 9/1979 | Mischo et al. | 250/561 |
| 4,611,907 | 9/1986 | Inatsuki | 355/41 |
| 4,691,112 | 9/1987 | Wydler | 250/570 |
| 4,705,958 | 11/1987 | Sugita | 250/578 |
| 4,724,463 | 2/1988 | Matsumoto | 355/29 |
| 4,746,020 | 5/1988 | Schenk | 209/3.3 |
| 4,864,149 | 9/1989 | Matsumoto | 250/561 |
| 4,906,854 | 3/1990 | Rauh et al. | 250/561 |
| 4,947,205 | 8/1990 | Benker et al. | 355/41 |

Primary Examiner—David C. Nelms
Assistant Examiner—K. Shami
Attorney, Agent, or Firm—Krass & Young

[57] ABSTRACT

A method and apparatus for determining the edge of an individual frame of photographic film on a strip of photographic film being moved along a photographic film transport path. A plurality of light sensors are positioned in a substantially linear array substantially perpendicular to and on one side of the path and a light is shined through the film toward the array of light sensors as the strip passes along the path. By sensing the level of illumination incident upon each of the sensors and comparing the level of illumination incident thereon with a predetermined level corresponding to a known degree of opacity associated with the interframe border between individual frames on the film, the presence of a film edge can be determined when the level of illumination associated with a predetermined number of tile sensors corresponds to a degree of opacity at least as great as the predetermined level. Also disclosed is a methodology for measuring the size and optical center of an image in an individual frame of photographic film by measuring the rate of change of sensed density of the film at a plurality of transversely spaced locations as the film is moved incrementally therepast.

9 Claims, 6 Drawing Sheets

METHOD AND APPARATUS FOR DETECTING FILM EDGES AND FILM OPTICAL CENTERS

RELATED APPLICATION

This application is a continuation-in-part of U.S. patent application Ser. No. 816,135, filed on Dec. 31, 1991, now abandoned, and entitled "Optical Film Border Sensor and Method of Detecting a Film Border."

FIELD OF THE INVENTION

The present invention relates to a method and apparatus for detecting information with respect to images on a photographic film strip for use in precise positioning of the images in a piece of photographic equipment.

BACKGROUND OF THE INVENTION

It has long been the practice of commercial photographers and photo-finishing studios to encode information about individual film negatives on the edge of the film. Encoding marks placed on the edge of the film are typically opaque markings, transparent markings, or machine readable holes punched in the film edge. These markings serve to identify the location of a particular frame of photographic film and may further comprise a pattern which is decodable to provide useful information to the photographer or photo finisher about the corresponding film exposure. With the advent of automated photographic film processing equipment, accurate detection and interpretation of such film edge marks has become more important. Further, increased processing speeds of commercial photographing equipment have strained the abilities of current technology to accurately detect and interpret these marks in the higher speed environments.

Two principal methods have been used for detecting and reading edge markings on photographic film. In one method, utilized solely for punch marked film, differential pressure switches are located on one side of the film strip, and high pressure air is directed to the opposite side of the same film. As the punched portion of the film passes by the differential pressure switch, the pressure from the opposing air activates the switch, causing it to close, thereby indicate the presence of a punched hole. However, differential pressure switch sensors are not capable of reading film that is merely marked. Further, at high speeds, punched holes pass the sensor orifice too quickly for the pressure switch to accurately record the change in pressure.

A second method currently in use is the optical sensor. In this method, a light source is used in combination with a photocell to detect the presence of markings as the film edge is passed between the light source and the photocell. Conventional cadmium sulfide photocells are capable of accurately detecting either holes or marks only when presented a high level of consistency in the photographic film substrate and dyes. Because such photocells have poor response times, however, this method is also limited in its inability to process film at high speed. A further drawback of this methodology is intolerance to variations in film size. Conventional film mark reading devices must be precisely positioned in relation to the film marks, and frequently malfunction if misalignment occurs. This problem is further exacerbated by variations in film tracking, as the strip of film moves through the processing equipment. Because the film is under only the minimum required tension as it moves on rollers, it is not unusual for the edge of the film to track laterally in relation to the conventional sensor.

The invention described in my co-pending U.S. patent application Ser. No. 639,566 entitled "Compensating Optical Sensor" provides an improved optical sensor and mounting means, which allows the sensor to move in relation to the photographic film, and which is dynamically responsive to changes in film density. The invention automatically adapts to variances in the base density of the film, thereby allowing either punched hole or photographic marks on the film to be accurately detected. The circuitry associated with the sensor automatically adjusts the sensitivity of the sensor based on the density of the film, and does so dynamically during film transport. Accordingly, the photographic sensor accurately detects and reads marks or punched holes, even though the photographic density within a single roll of film may vary substantially. No recalibration of the sensor is required when different types of marking, or different types of film are presented to the processing equipment.

In spite of the improvements that I have made in devices adapted to reach such markings disposed along the edge of the photographic film strip, the reading of such marks inherently complicates and slows automated film processing. Further, additional and time consuming steps are required to place the markings on the edge of the photographic film. Thus, the steps necessary for placement, detection and subsequent interpretation of such markings strain the abilities of current technology for automated high speed photographic film processing environments.

One embodiment of the present invention is designed to eliminate, or at least minimize, the necessity for use of markings on the edge of the film to identify individual frames of photographic film. Therefore, the present invention eliminates the necessity for the steps of placement, detection and subsequent interpretation of such markings.

A further embodiment of the present invention is designed to measure the size and optical center of an image in an individual frame of photographic film on a strip of photographic film.

SUMMARY OF THE INVENTION

One aspect of the present invention provides a method of determining the location of an individual frame of photographic film on a strip of photographic film being moved along a photographic film transport path without the use of marks placed along the edge of the film. A plurality of light sensors are positioned in a substantially linear array substantially perpendicular to and on one side of the path. Light is directed through the film toward the array of light sensors as the strip passes along the path. The level of illumination incident to each of the sensors is sensed and compared to a predetermined level of illumination corresponding to a known degree of opacity associated with the interframe border (i.e., the border between individual frames on the film). It is not likely that images exposed on the frame will produce a uniform degree of opacity for all of the active sensors. Thus, the location of a film frame edge can be determined when the interframe border causes the active sensors to detect a degree of opacity corresponding to the predetermined level.

In one preferred embodiment, at least eight light sensors are positioned in a spaced apart substantially linear array dimensioned to correspond with the negative image area of 70 mm photographic film. The level of illumination incident on all of the sensors is then compared with the predetermined level for use in scanning 70 mm photographic film. Alternatively, the level of illumination incident upon only a predetermined number of sensors may be compared with the predetermined value when scanning a smaller photographic image area, such as that associated with 35 mm film. A predetermined number of sensors may also be used where non-linear frame edges are likely to be encountered, such as in oval framed portrait exposures.

The method is adapted to position an individual frame of film in a piece of photographic equipment by determining the position of the center of the individual frame and the distance to the piece of photographic equipment. The leading edge of an individual frame of film can be determined at the point of transition of the level of illumination from a degree of opacity at least as great as the predetermined level. Further, the trailing edge of an individual frame of film can be determined at the point of transition of the level of illumination toward a degree of opacity at least as great as the predetermined level. In situations where the width of the film frames are constant (such as with 35 mm film), the center of the individual frame of film can be determined from the position of at least one film edge. When the width of each frame of film may vary, the center of the individual frame may be determined from the positions of the leading and trailing edges.

Essentially, the present method establishes at least one intensity parameter for each sensor corresponding to a known degree of opacity of the interframe border of the film. The light intensity from each sensor is compared to the established intensity parameters and an electronic signal is transmitted when a predetermined number of the compared values are at least as great as the established parameters. The electronic signal can be used to identify the position of the edges and center of the frame by signaling metering drive rollers, or other tracking systems. Thus, the present method selects at least one of the sensors and senses the intensity of light transmitted through the film by operation of the selected sensor for comparison purposes. This selection can be based on the type of film of frames to be encountered as previously described.

The present invention also encompasses an optical sensor device for determining the edge of an individual frame of photographic film on a strip of photographic film in a photographic printing mechanism operative to move the photographic film along a predetermined path for use in the inventive methodology. The apparatus includes an illumination device disposed on one side of the path and a plurality of light sensors disposed in a substantially linear array proximate to the illumination device on the opposite side of and substantially perpendicular to the path. A comparing device operates to compare the level of illumination incident upon each of the sensors with a predetermined level corresponding to a known degree of opacity so as to determine the presence of a film edge when the level of illumination corresponds with a predetermined number of the sensors as previously described.

According to another aspect of the invention a method is provided for measuring the size and optical center of an image in an individual frame of photographic film on a strip of photographic film adapted for movement along a photographic film transport path.

The method according to this aspect of the invention comprises moving the strip of film along the path; at a sensor workstation along the path continuously incrementally measuring the density of the film moving therepast at a plurality of locations spaced transversely across the path to generate a plurality of density values for each incremental measuring location on the film; measuring the rate of change of density at each transverse location by comparing successive incremental values at that location; comparing the rate of change of density at each transverse location to predetermined rate of change thresholds to identify transition areas on the film and generate transition area information and transmitting the transition area information to film processing equipment for use in locating film edges, splices, and images. This methodology allows the size and optical center of an image to be determined without reference to film borders or film edges.

According to a further feature of the invention methodology the method includes the further step of adapting the threshold values based on operational information generated in carrying out the methodology. This aspect of the invention methodology allows the threshold value to be adaptively modified to compensate, for example, to changes in film density.

DETAILED DESCRIPTION OF THE PREFERRED EMBODIMENT

Figure 1:
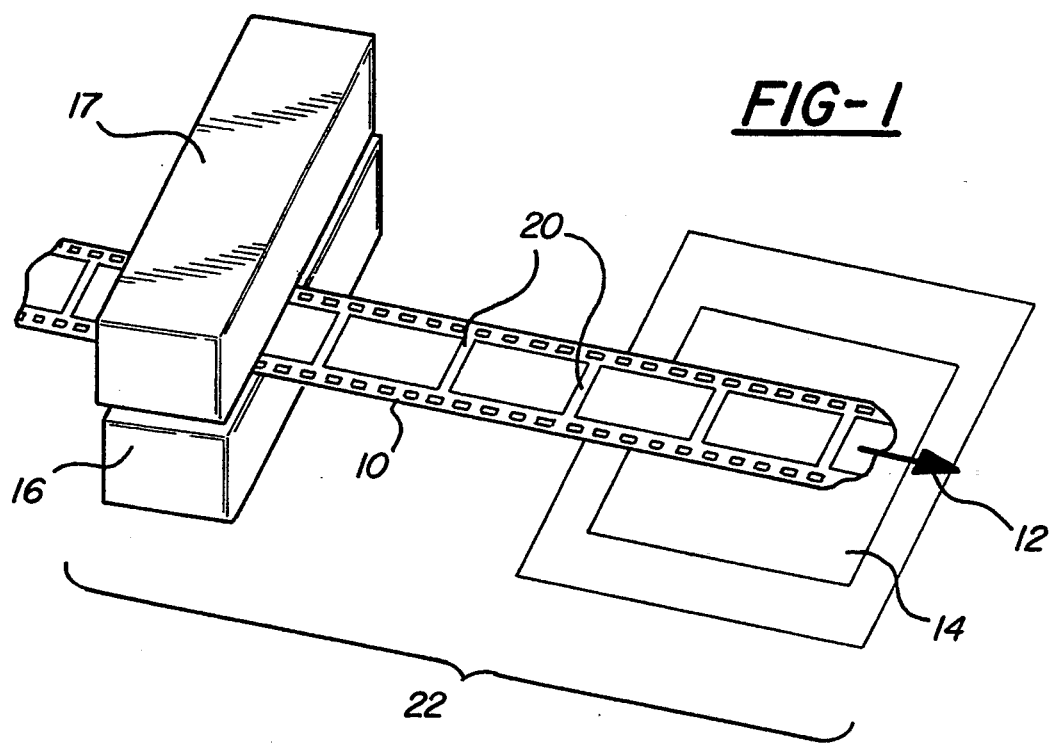
FIG. 1 is a perspective view of a sensor according to a first embodiment of the present invention showing the operation of the sensor in relation to a film strip and a piece of photographic equipment.

The present invention provides a sensor device for detecting information with respect to images on a photographic film strip for use in precise positioning of the images in a piece of photographic equipment.

With reference to FIGS. 1-6, the photographic printer is generally operative to move the photographic film 10 along a predetermined path 12 for processing on an optical stage 14 therein. The inventive optical sensor apparatus generally includes an illumination device 16 disposed on one side of tile path and a light sensor device 17 disposed proximate to the illumination device on the opposite side of the path 12. The optical sensor 17 is adapted to locate the interframe borders 20 on the photographic film 10 and by doing so, locating the edges of the frame thereon. By determining this information, the center of the frame can be located (i.e., half way between the edges) and the frame accurately positioned on the optical stage 14 of the printer by knowing the distance 22 between the sensor and the optical stage.

Figure 2:
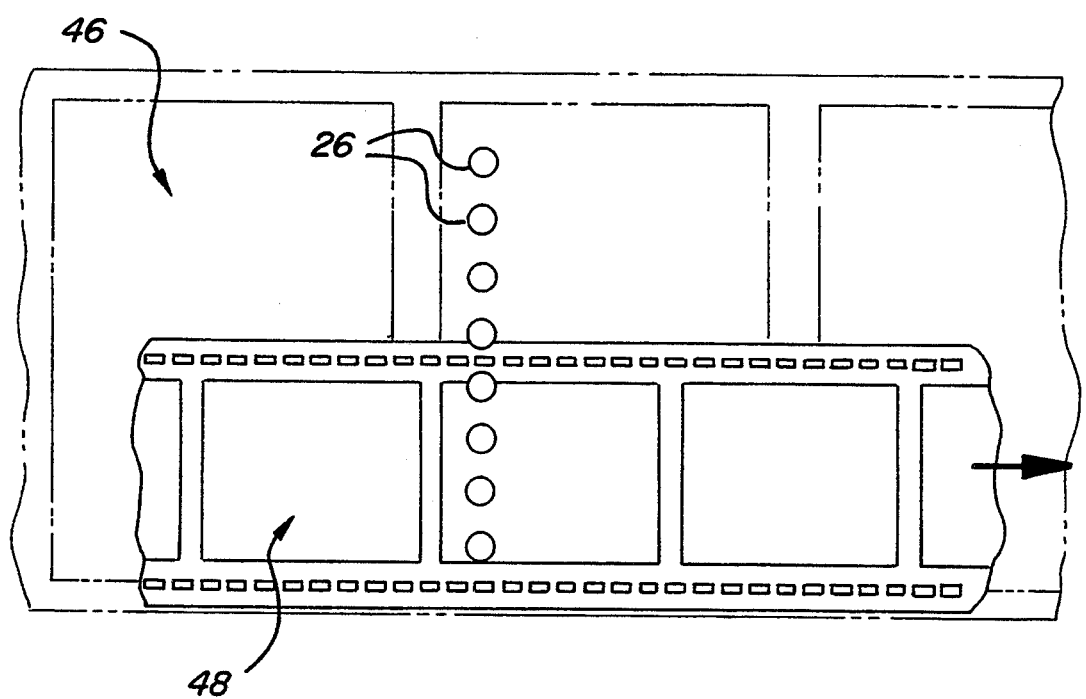
FIG. 2 is a diagram of the configuration of a sensor array in the sensor system of FIG. 1 in relation to various sizes of negative film.
Figure 3:
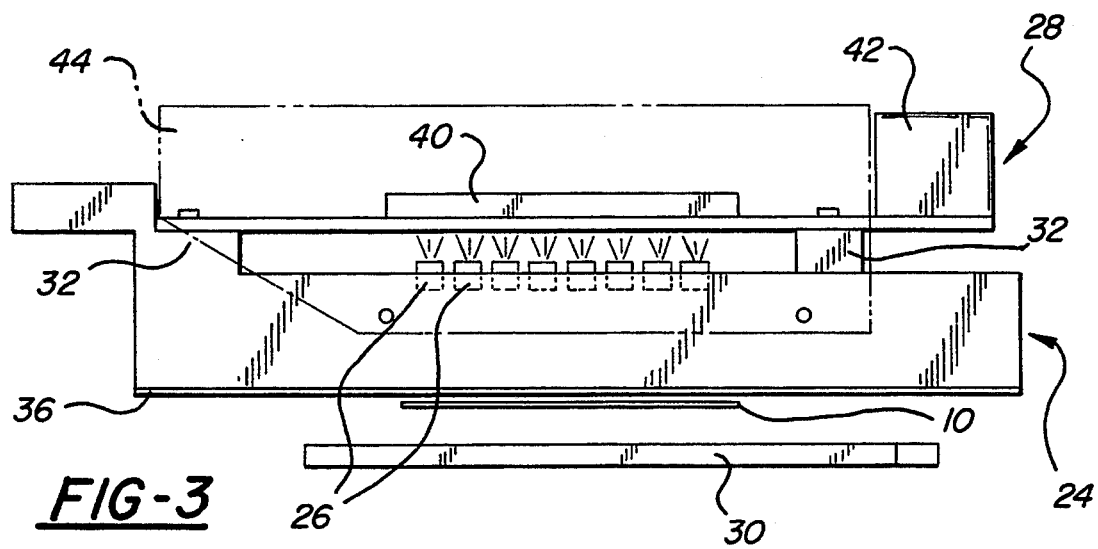
FIG. 3 is a side cross-sectional view of the sensor system of FIG. 1.
Figure 4:
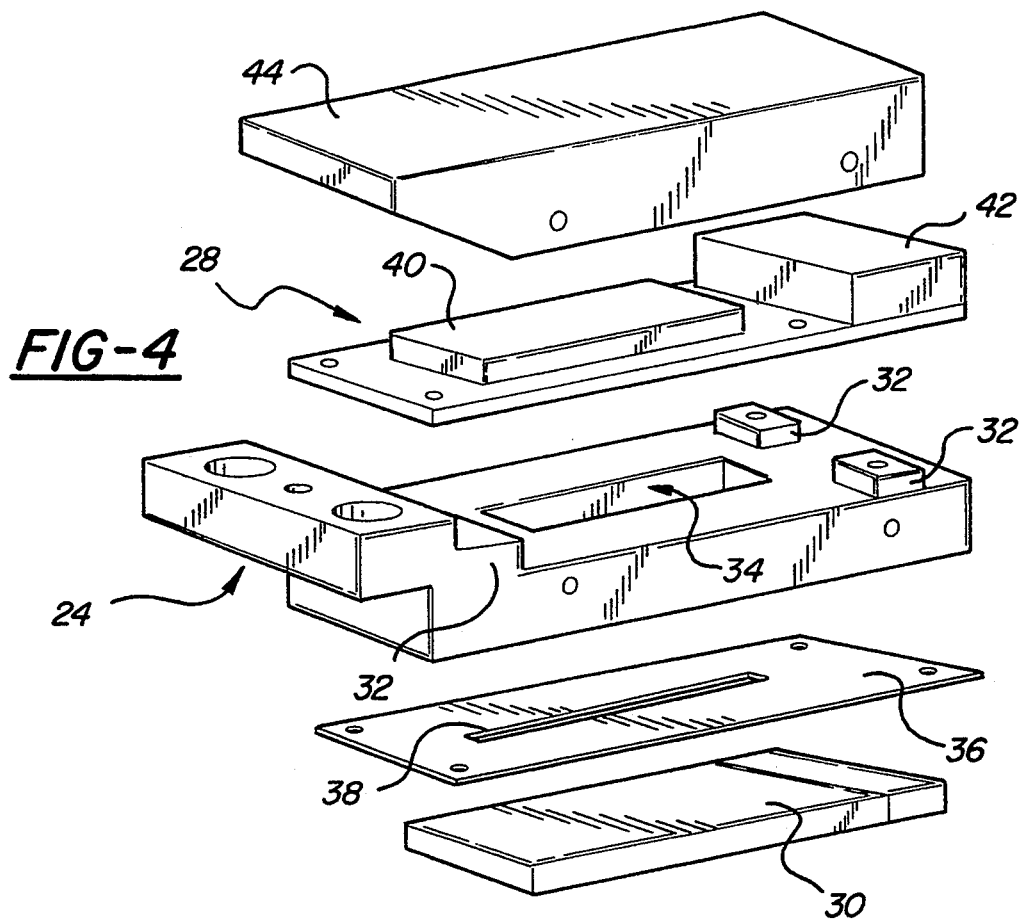
FIG. 4 is an exploded perspective view of the sensor system of FIG. 1.

More specifically and with reference also to FIGS. 2 through 4, the sensor apparatus of the present apparatus includes a support base 24 adapted to position a plurality of light sensors 26 in a linear array mounted on a circuit board 28. The base 24 includes a plurality of spacers 32 which operate to position the sensors 26 within a throughhole 34 in the base 24 when the circuit board 28 is attached to the base 24. The circuit board 28 provides the platform for mounting the necessary circuitry 40 and connector 42 for the operation of the plurality of light sensors 26. A cover 44 is secured to the base 24 to enclose the optical sensor mechanism during use.

In use, the assembled optical sensor is positioned on one side of the film 10. A light source 30, such as an electroluminescent tape strip or bulb, directs light through the film 10, through the slot 38 in the base plate 36, and onto the light sensors 26. Eight light sensors are positioned in linear array which dimensionally corresponds to the image size of 70 mm film 46. All eight sensors may be used for 70 mm film or a selected subplurality of light sensors may be used to correspond to smaller film sizes, such as four sensors corresponding to 35 mm film 48.

Figure 5:
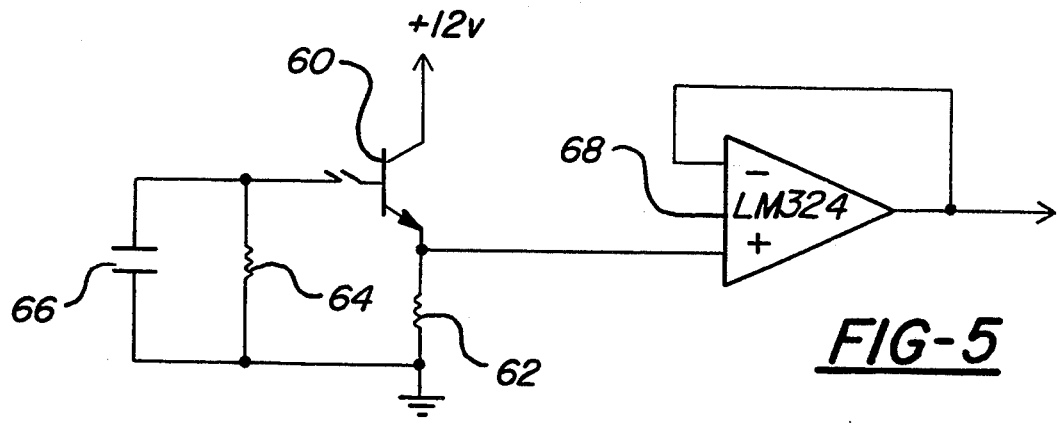
FIG. 5 is a schematic view of circuitry for a single sensor of the FIG. 1 embodiment.
Figure 6:
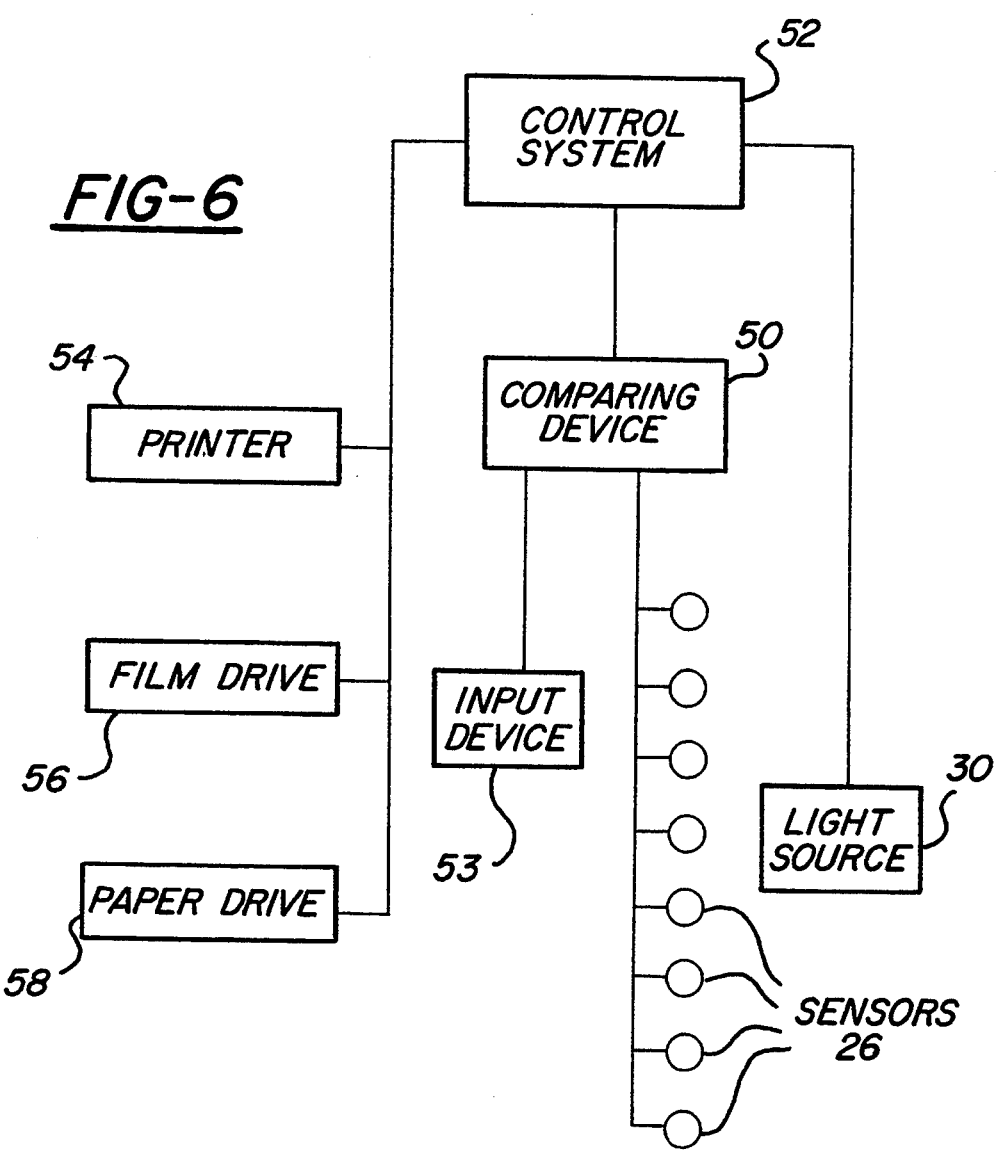
FIG. 6 is a diagram of the control mechanism for the sensor system of FIG. 1.
Figure 7:
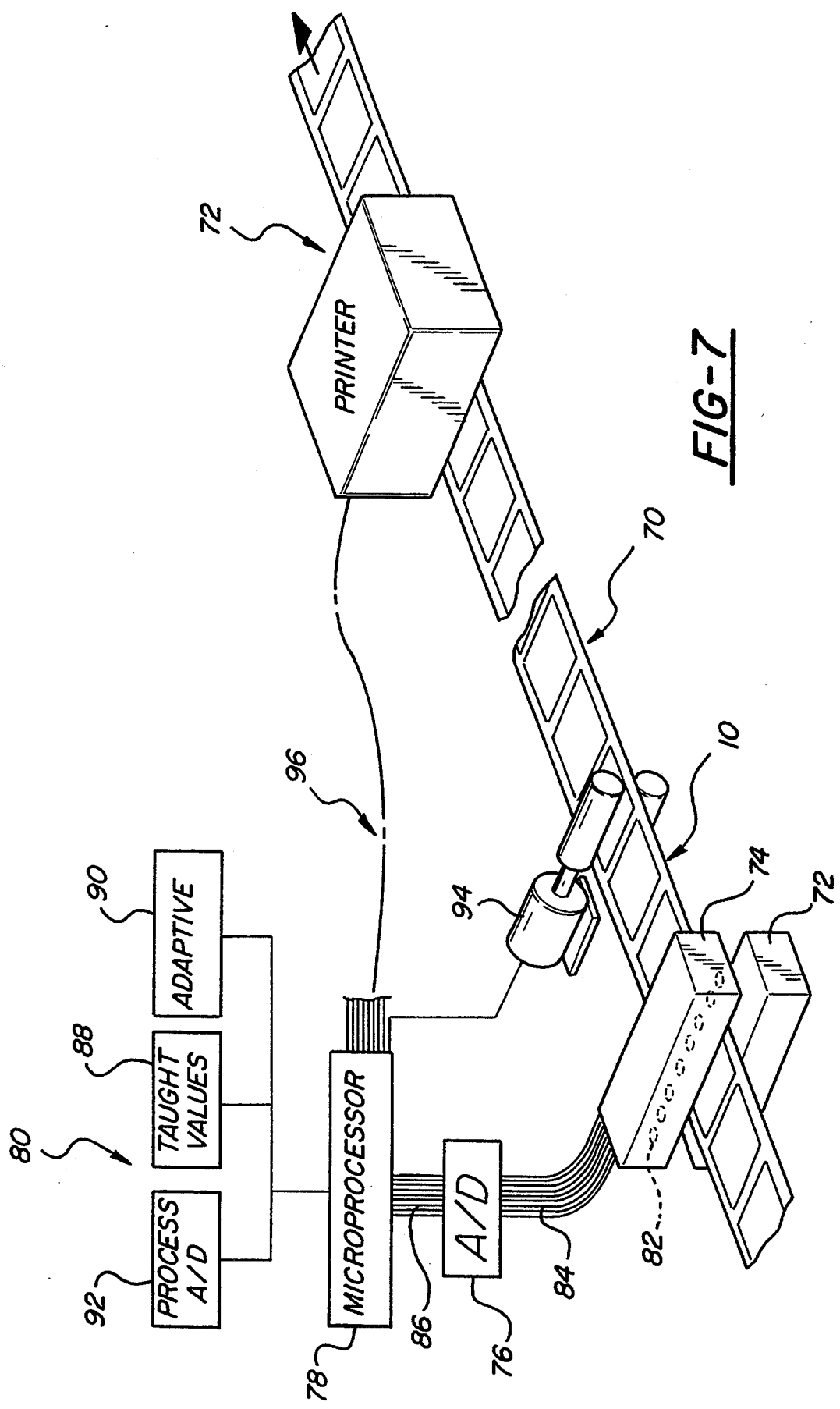
FIG. 7 is a perspective diagrammatic view of a second embodiment of the invention sensor.

With reference also to FIGS. 5 and 6, a comparing device 50 is electronically linked into the photographic printer control system 52. It compares the level of illumination incident upon each of the sensors 26 being utilized with a predetermined level. This predetermined value corresponds to the known degree of opacity found on the interframe border of the film. A film edge is detected when the level of illumination associated with the active sensors 26 corresponds to the degree of opacity of the predetermined level. An input device 53, such as a keyboard or other more automated devices, is utilized to establish the various parameters under which the operations occur. For example, the predetermined level of opacity may be set by positioning an interframe border between the sensor 26 and light 30 and activating the comparing device to determine the level of opacity associated therewith. Further, the identity of the sensors 26 being used may be manually entered or automatically detected from the size of the film being used.

The comparing device is further configured to send a signal to the overall control system 52 when the level of opacity sensed corresponds to the predetermined level. The control system 52 can then use this information in controlling the various printer components, such as the printer 54, film drive 96, and paper drive 58, to determine the edges and center of the frame and position them for photographic printing operations.

The sensors 26 require sufficient circuitry to provide a coordinated signal in response to light incident thereon. An example of such a circuit for a single sensor is shown in FIG. 5. A phototransistor 60 is connected to 1M ohm resistors 62,64 and a 100 pf of capacitor 66 as shown to regulate the amount of light necessary to turn on phototransistor 60. Voltage follower 68 buffers the signal from the phototransistor 60. Other known circuits to produce a buffered voltage signal in response to incident light may also be used.

The previously described apparatus may be used to determine the edge of an individual frame of photographic film on a strip of photographic film being moved along a photographic film transport path. Light shines through the film toward the plurality of light sensors which are positioned in a substantially linear array substantially parallel to the interframe borders and on one side of the strip. The level of illumination incident upon each of the sensors is sensed and compared to the predetermined level. The film edge is present when the level of illumination associated with a predetermined number of the sensors corresponds to a degree of opacity at least as great as the predetermined level.

More specifically, the leading edge of an individual frame of film is present at the point of transition of the level of illumination from a degree of opacity at least as great as the predetermined level. Conversely, the trailing edge of an individual frame of film is present at the point of transition of said level of illumination to a degree of opacity at least as great as the predetermined level. When using film having constant frame widths, the center of the individual frame of film can be determined from the position of either film edge. When the width of the film may vary, the center of the individual frame may be determined from the positions of both the leading and trailing edges. Thus, the present method can be utilized to position the individual frame of film in a piece of photographic equipment by knowing the position of the center of the individual frame and the distance to the piece of photographic equipment.

The sensor system of the embodiment of FIGS. 7-10 is intended for use in situations where there is need to detect the edges or borders of individual frames of film and also need in certain situations to detect the size and optical center of the image in the frame irrespective of the edges of the frame.

The sensor system of FIGS. 7-10 is used in association with photographic film 10 arranged to be moved along a path 70 for subsequent processing by processing equipment such as a printer 72.

The sensor system includes an illumination device 73 positioned below the path 70; a light sensor 74 positioned above the path 70 in vertical alignment with the illumination device 73; an analog to digital converter 76; a microprocessor 78; and software 80.

Illumination device 73 and light sensor device 74 may be identical to the illumination device 16 and light sensor device 17 of the FIGS. 1-6 embodiment and, as such, the illumination device 73 may comprise an electroluminescent tape strip or bulb which directs light upwardly through the film 10 into sensor device 74 where the light is sensed by eight light sensors 82 positioned in linear array across the film path. As with the FIGS. 1-6 embodiment, all eight sensors may be used for 70 mm film or a selectively subplurality of light sensors may be used to correspond to smaller film sizes such as four sensors corresponding to 35 mm film. The eight sensors are each provided with a lead 84 extending to analog to digital converter 76 and it will be understood that each sensor provides a signal on the corresponding lead 84 corresponding to the level of illumination incident on that sensor at any point in time with the level of illumination on any particular sensor varying in accordance with the density or opacity of the film 10 passing therebeneath. Following conversion to a digital signal by converter 76, the signal from each sensor is transmitted to microprocessor 74 by an individual lead 86 where it is processed and analyzed in accordance with software 80.

Software 80 includes a program 88 of taught values, a program 90 of adaptive values, and a program 92 for general processing and control of the system.

Program 88 includes taught values for each sensor. Specifically, program 88 includes, for each sensor, information with respect to what is black, what is white, and what is a base density for each sensor. These values may be taught by covering each sensor to teach black, showing the sensor unexposed but processed film to teach the base density, and uncovering the sensor to teach white.

The adaptive program 90 is operative to observe and receive operational information as the film is moved through the sensor system and to utilize the information thus learned to adaptively vary the stored density information. For example, program 90 may continuously observe the base density readings being received as the film is moved incrementally past the sensor and maintain a running average of base film densities so that the stored base film densities for reference purposes is always equal to an average of base densities recorded over the last X number of incremental moves of the film through the system.

For example, the motor 94 driving the film and controlled by the microprocessor 78 and may operate to move the film incrementally 2000 times per second with each move comprising 0.0025 inches so that the film moves along path 70 at the rate of 5 inches per second. Adapter program 90 may contain a running average of base film densities equal to the average of the last 100 measurements occurring in response to the last 100 incremental moves of the film through the system.

Program 92 may include, inter alia, a low pass filter and a high pass filter operative to illuminate spikes on both the high and low ends of the base film density averages.

In operation, as the film 10 is moved along path 70 incrementally by a motor 94 (for example, at 2000 increments per second with each incremental move comprising 0.0025 inches), each sensor 82 (or a subplurality of sensors in the case where the film width is less than the maximum width for which the system is designed) transmits an analog signal on its respective lead 84 corresponding to the level of illumination incident on the sensor for each increment of movement of the film therepast with the level of illumination representing the relative opacity or density of the film since the illumination is in proportion to the amount of light passing through the film from the illumination device 73.

The analog illumination signals from each active sensor are converted to a digital signal by converter 76 whereupon they are fed to microprocessor 78 through leads 86. In the microprocessor, operating in association with the software 80, rapidly successive density readings from each sensor are inputted and the rate of change of density $d_d/d_t$ at each sensor is calculated and this rate of change information is transmitted, either directly or via a storage device, on leads 96 to printer 72 where the information is utilized by the printer to locate the start and finish, and thereby the optical center, of each image on each :frame of the film 70 so as to facilitate tile printing of prints from each negative. The operation of the device is further seen in FIGS. 8–10.

Figure 8:
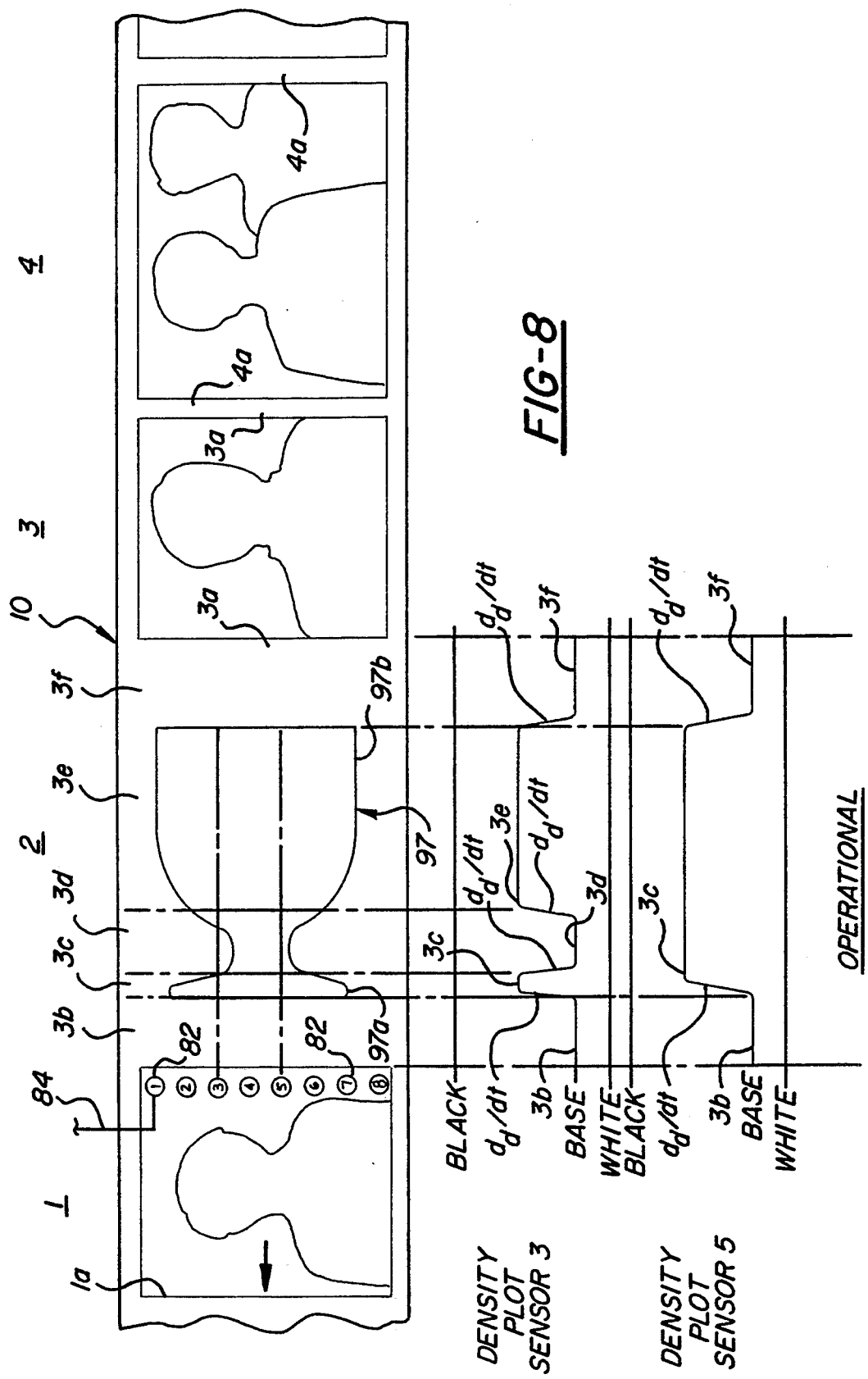
FIGS. 8, 9, and 10 are schematic views illustrating the operation of the sensor of FIG. 7.

In FIG. 8 the film strip 10 is illustrated as including a plurality of frames including a relatively square frame 1 having well defined borders 1A, a relatively elongated frame 2 having no borders and including tile image, for example, of a wine glass 97; a relatively square frame 3 having well defined borders 2A; and a relatively elongated frame 4 having well defined borders 4A.

The invention sensor functions to determine the edges or borders of the well defined frames 1, 3, and 4 and, additionally, functions to determine the size and optical center of the wine glass image 97 of the frame 2 despite the fact that the frame 2 has no defined or ascertainable edges or borders.

Specifically, and with reference to the density plots for sensors or channels 3 and 4 as the wine glass image 97 is moved incrementally past the sensors 82, the density plot for sensor 3 initially shows a base density 3B corresponding to the base density area 3B of the frame 3, whereafter, upon encountering the base 97a of the wine glass image, the density increases sharply to a value of 3C whereafter, as the base moves past the sensor into the base film area 3D the reading drops again to the base level whereafter, as the bowl 97b of the wine glass image is encountered the density reading again rises to a level 3E and remains at that level until the end of the bowl is reached and the reading again drops down at 3F to the base density level. At each point as the wine glass image moves through the sensor, the absolute successive values of the film density are inputted and, utilizing the software 80, the rate of change of density $d_d/d_t$ is calculated. This rate of change information is the information transmitted from the microprocessor on leads 96. The rate of change information leaving the microprocessor 78 is in each case based on a comparison of the rate of change of density information being received by the microprocessor from each sensor and threshold rate of change of density parameters provided by the software so that, at any given point in the incremental movement of the film through the sensor system, no rate of change information signal is provided on the corresponding lead 96 leaving the microprocessor unless and until the rate of change of density $d_d/d_t$ occurring at that sensor at that time exceeds the established rate of change threshold or parameter determined by the software.

Since the invention system is not dependent on detecting the presence and location of borders or edges, the system can measure images, such as the wine glass of frame 2, that have no well defined borders and locate the size and optical center of the image. The system is also able to locate the optical center of framed images of varying sizes and configurations, as seen by a comparison of the images 1, 3, and 4, since as to each frame the system is not relying on the sensing of the edges or borders but rather is sensing the size and distribution of the image in the frame and thereby providing information sufficient to locate the optical center of the image for use by the subsequent processing equipment such as the printer 72.

Figure 9:
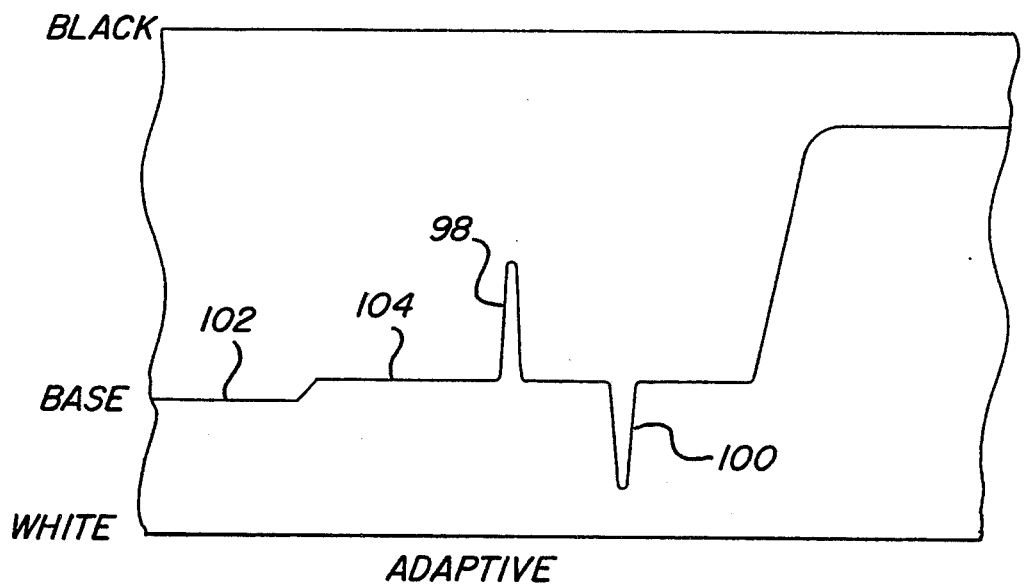

Adaptive program 90, as seen in FIG. 9, is also operative to eliminate high pass spikes such as seen at 98 and low pass spikes such as seen at 100 and is further able to adaptively change the base density level in response to the information received during the operation of the system.

For example, the base density level may start out at a level 102 but may thereafter be raised to a level 104 based on the adaptive program 90 looking at the base density information received over the last x number of incremental movements of the film through the sensor and adaptively modifying the average density to reflect the most recent density experience of the system so that the base density thresholds, and thereby the rate of change density thresholds, against which the incoming density signals from each of the sensors is being measured is constantly being adaptively revised to reflect the operational conditions of the system. For example, the base density may change for different types of film being processed by the system or may change even with the same film being processed by the system because of variations in the density of any given film being processed by the system.

Figure 10:
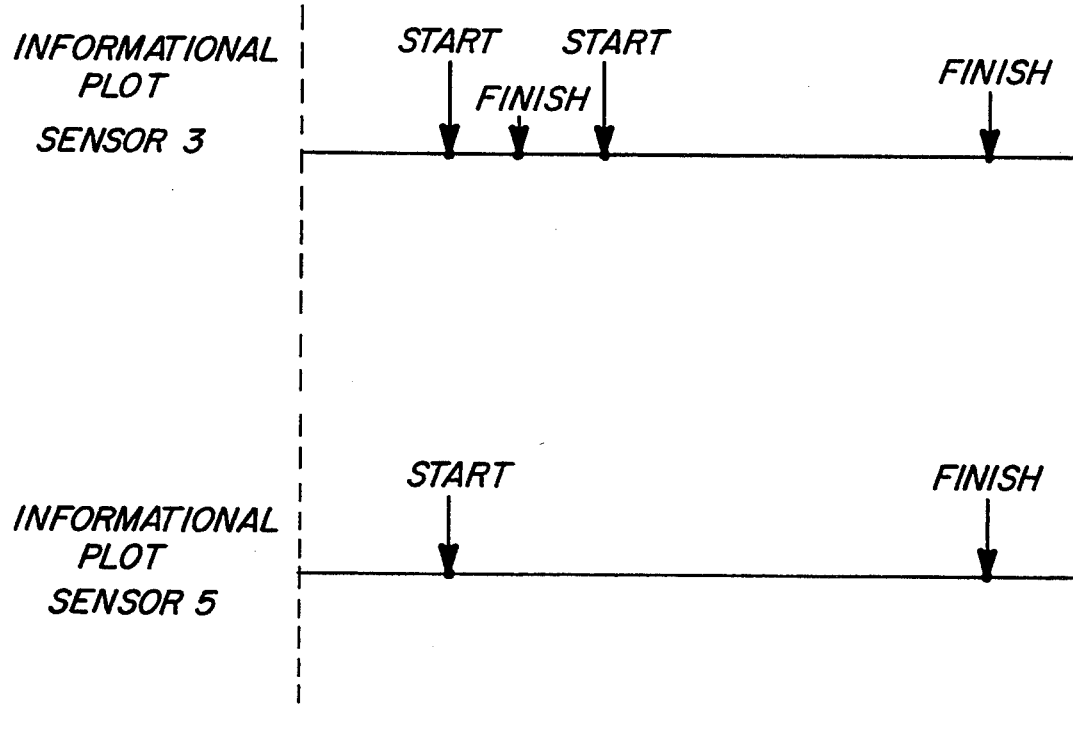

The final informational plot determined by the system is illustrated in FIG. 10 wherein informational plots for sensors 3 and 5 are shown corresponding to the density plots for sensors 3 and 5 as seen in FIG. 8.

Thus, for sensor 3, the information being provided by the microprocessor 76 on the corresponding lead 96 for transmittal to the subsequent processing equipment (such as printer 22) shows an image start signal at the point of high, above threshold density rate of change occurring as the sensor encounters the beginning of the base 97a of the wine glass image; a finish signal at the point of high, above threshold density rate of change occurring as the image base 97a moves past the sensor; a further start signal at the point of high, above threshold density rate of change occurring when the bowl 97a of the wine glass image is encountered; and a further finish signal at the point of high, above threshold density rate of change occurring when the bowl 97a of the wine glass image moves finally past the sensor. Similarly, the information being provided by the microprocessor on the line 96 corresponding to the sensor or channel 5 shows a high rate of change of density start signal at the point where the sensor encounters the beginning of the base 97a of the wine glass image and a high rate of change of density finish signal at the point where the top of the bowl 97b of the wine glass image passes through and beyond the sensor location.

It will be understood that the remaining sensors that are exposed to the film will also generate density plots of the type seen in FIG. 8 for sensors 3 and 5 and will further generate informational plots similar to the informational plots seen in FIG. 10 for sensors 3 and 5 so that the processing equipment 72 at all times receive a plurality of channels of information from the active sensors, which information is utilizable by the equipment 72 to determine the size, shape and optical center of the image in each frame of the film as the film is processed by the equipment 72.

The sensor systems of FIGS. 7-10 will be seen to be capable of measuring images, as well a film borders, and to function by comparing the rate of change of density at each sensor location to predetermined rates of change of density thresholds so as to identify transition areas on the film and generate transition area information for transmittal to film processing equipment for use in locating film borders, splices, images, and the like. The system of FIGS. 7-10 will further be seen to function to continuously monitor the received operational information and modify or adapt the parameters of the software to the received operational information so that the threshold values provided by this software for use comparing tile rate of change of density at the sensors to predetermined threshold rates is constantly being adapted to reflect instantaneous operational conditions of the apparatus.

From the foregoing description of the preferred embodiments it can be seen that various alternative embodiments of the invention can be anticipated without departure from the scope of the invention as defined in the following claims.

I now claim:

1. A method of determining the optical center of an individual frame of photographic film on a strip of photographic film being moved along a photographic film transport path, comprising the steps of;
   positioning a plurality of light sensors in a substantially linear array substantially perpendicular to and on one side of said path at a sensor location along said path;
   passing the strip of film along said path;
   shining light through said film toward said array of light sensors as said strip is moved along said path;
   sensing the level of illumination incident upon each of said sensors;
   comparing the level of illumination incident upon said sensors with a predetermined level corresponding to a known degree of opacity associated with the interframe border between individual frames on the film;
   as the leading edge of an individual frame of the film reaches the sensing location, determining the arrival of the leading edge of the individual frame at the sensor location by determining when the level of illumination associated with a predetermined number of said plurality of sensors corresponds to a degree of opacity at least as great as said predetermined level;
   as the trailing edge of the individual frame reaches the sensor location, determining the arrival of the trailing edge of the individual frame at the sensor location by determining when the level of illumination associated with the predetermined number of said plurality of sensors corresponds to a degree of opacity at least as great as said predetermined level; and
   determining the center of said individual frame of film from the position of said leading end trailing edges.

2. The method of claim 1, wherein said method further comprises a method for positioning the individual frame of film in a piece of photographic equipment utilizing the determined position of the center of the individual frame and the distance to the piece of photographic equipment.

3. The method of determining the optical center of an image defined within an individual frame on a continuous roll of photographic film, comprising:
   illuminating a first side of said film;
   sensing the intensity of light transmitted through said film by a plurality of light sensors disposed in a linear array on a second side of said film opposite said first side of said film at a sensor location along a film path;
   establishing at least one intensity parameter for each said sensor, each of said at least one intensity parameters corresponding to a known degree of opacity of said film;
   moving the film along said film path and past said sensor location;
   as the individual frame of film is moved along the film path and past the sensor location to move the image contained therein past the sensor location, continuously comparing said light intensity from each said sensor to said established intensity parameters and detecting first the arrival of the starting edge of the image and thereafter the arrival of the finish edge of the image by noting as to each arrival when a predetermined number of said compared values is at least as great as said established intensity parameters; and determining the optical center of said image from the position of the starting and finish edges of the image.

4. The method of claim 3 wherein the method further comprises a method for positioning the individual image in a piece of photographic equipment utilizing the determined position of the optical center of the image and the distance to the piece of photographic equipment.

5. A photographic apparatus for determining the optical center of an individual frame of photographic film on a strip of photographic film and moving the film along a predetermined path to the center of the optical stage of a photographic printer, said apparatus comprising:

an illumination device disposed on one side of said path at a sensor location along said path spaced from the center of the optical stage of the optical printer by a distance greater than one-half of the width of the individual frame;

a plurality of light sensors disposed at said sensor location in a substantially linear array proximate to said illumination device on the opposite side of said path and substantially perpendicular to said path; and control means operative to compare the level of illumination incident upon each of said sensors with a predetermined level corresponding to a known degree of opacity, to determine the presence of the leading edge of the individual frame by noting when the level of illumination associated with a predetermined number of said plurality of sensors corresponds to a degree of opacity at least as great as said predetermined level, to thereafter determine the presence of the trailing edge of the individual frame by noting when the level of illumination associated with a predetermined number of said plurality of sensors again corresponds to a degree of opacity at least as great as said predetermined level, and to determine the center of said individual frame of film from the determined position of the leading and trailing edges of the frame.

6. A method of measuring the size and optical center of an image in an individual frame of photographic film on a strip of photographic film adapted for movement along a photographic film transport path, comprising the steps of:

moving the strip of film along said path;

at a sensor location positioned along said path, continuously and incrementally measuring the density of the film moving therepast at a plurality of locations spaced transversely across the path to generate a plurality of density values for each incremental measuring location on the film;

measuring the rate of change of density at each transverse location by comparing successive incremental values at that location;

as the image moves past the sensor location, continuously comparing the rate of change of density at each transverse location to predetermined rate of change thresholds to identify transition areas on the film corresponding to the starting edge and the finish edge of said image and generate transition area information; and transmitting the transition area information to film processing equipment for use in locating the optical center of the image based on the identified starting edge and finish edge of the image.

7. A method according to claim 6 wherein:

said method includes the further step of adaptively varying the predetermined rate of change threshold values based on operational information generated in carrying out the method of claim 6.

8. A method according to claim 6 wherein the step of measuring the density of the film includes:

positioning a plurality of light sensors respectively at each transverse location;

shining light through said film toward said light sensors; and sensing the level of illumination incident upon each sensor.

9. A method according to claim 8 wherein:

the step of measuring the rate of change of density at each transverse location comprises measuring the rate of change of the level of illumination incident on the sensor positioned at that transverse location.

* * * * *